United States Patent
Allard et al.

(10) Patent No.: US 7,657,383 B2
(45) Date of Patent: Feb. 2, 2010

(54) METHOD, SYSTEM, AND APPARATUS FOR COMPACTLY STORING A SUBJECT GENOME

(75) Inventors: David J. Allard, Boynton Beach, FL (US); Robert M. Szabo, Boca Raton, FL (US)

(73) Assignee: International Business Machines Corporation, Armonk, NY (US)

( * ) Notice: Subject to any disclaimer, the term of this patent is extended or adjusted under 35 U.S.C. 154(b) by 442 days.

(21) Appl. No.: 10/856,600

(22) Filed: May 28, 2004

(65) Prior Publication Data

US 2005/0267693 A1 Dec. 1, 2005

(51) Int. Cl.
*G06F 19/00* (2006.01)
(52) U.S. Cl. .................................................. 702/20
(58) Field of Classification Search ................... 702/20
See application file for complete search history.

(56) References Cited

U.S. PATENT DOCUMENTS

| | | | |
|---|---|---|---|
| 5,032,502 A | 7/1991 | Stodolsky | |
| 5,976,790 A | 11/1999 | Pinkel et al. | |
| 6,335,167 B1 | 1/2002 | Pinkel et al. | |
| 7,157,228 B2 * | 1/2007 | Hashmi et al. | 435/6 |
| 2002/0064792 A1 | 5/2002 | Lincoln et al. | |
| 2002/0192699 A1 | 12/2002 | Zhang et al. | |

OTHER PUBLICATIONS

Delcher et al. "Alignment of Whole Genomes," Nucleic Acids Research (1999) vol. 27, No. 11, pp. 2369-2376.*
Chen, X., et al., "A Compression Algorightm for DNA Sequences & Its Applications in Genome Comparison", City Univ. of Hong Kong. (1999).
Sato, H., et al., "DNA Data Compression in the Post Genome Era". Genome Informatics, No. 12, pp. 512-514, (2001).
Fashing, M., et al., "Compressing & Searching Genomic Sequence Data", Checkpoint 1 and 2, Duke University, (Spring 2002).

* cited by examiner

*Primary Examiner*—Jerry Lin
(74) *Attorney, Agent, or Firm*—Novak Druce + Quigg

(57) ABSTRACT

A method of representing a subject genome can include comparing the subject genome to a base reference genome and identifying a difference between the subject genome and the base reference genome. The method can further include assigning one or more items of descriptive information to the difference, and compiling the items into a data set, where the data set represents the subject genome.

19 Claims, 3 Drawing Sheets

METHOD, SYSTEM, AND APPARATUS FOR COMPACTLY STORING A SUBJECT GENOME

BACKGROUND

1. Field of the Invention

The present invention relates to the storage of a subject genome.

2. Description of the Related Art

A genome is comprised of an organism's complete set of deoxyribonucleic acid (DNA). DNA in the human genome is comprised of 22 pairs of chromosomes and 2 sex chromosomes. Each chromosome consists of many genes, which are the functional and physical units of heredity passed from parent to offspring. Researchers call determine what kind of illnesses a person may be predisposed to by studying the genes contained within the individual's genome. For example, a number of genes have been identified and associated with breast cancer, muscle disease, deafness, and blindness. Early detection of disease can lead to an understanding of how a specific medicine will work on an individual, allow doctors to design drug treatments that are specifically customized to an individual's unique genome, assist in the development of effective new therapies, and even lead to early intervention for chronic illnesses.

In order to analyze the biological properties of a gene, however scientists must further break the gene into its component parts, or nucleotide bases. A nucleotide base consists of one base chemical, namely, adenine, thymine, guanine, and cytosine. Every nucleotide base further consists of an additional molecule each of sugar and phosphoric acid. Notably, a gene is comprised of a specific sequence of nucleotide bases. or nucleotide sequences, that encode instructions on how to make proteins. Approximately 2% of a human genome is comprised of genes, while repeated nucleotide sequences which do not code for proteins ("junk DNA") make up at least 50% of the human genome. The remainder consists of non-coding regions whose functions are still unclear, but may provide chromosomal structural integrity and regulate the manufacture of proteins. Researchers analyze DNA sequence patterns within the genome in order to identify human genes and interpret their functions. For example, human genes appear to be concentrated in random areas along the genome, with vast expanses of non-coding DNA in between.

The problem faced by modern genomic research is that the amount of memory space required to store a representation of an individual human genome for research purposes is daunting. For example, the human genome contains over 3 billion nucleotide bases, and approximately 30,000 genes. Current methods of compressing genomic data include representing individual nucleotide bases using a 2-bit code, which can reduce the storage requirement from 3 billion characters to 750,000,000 characters. A further reduction of approximately 10 to 20% can be accomplished by accounting for repeated sequences of nucleotide bases, thereby reducing the storage requirement to about 600,000,000 characters. However, even with the reduction, this represents a formidable amount of data to store and process per individual genome.

SUMMARY OF THE INVENTION

The present invention provides a method, system, and apparatus for compactly storing a subject genome. More specifically, the subject genome can be represented as the set of differences between the subject genome and a base reference genome. The invention can compare the subject genome to a benchmark base reference genome. Further, the invention can assign items of descriptive information to each identified difference, such as a position reference point, an offset, and a text description of the difference. Accordingly, the invention can compile the items of descriptive information into a single data set. The data set can be stored in a data store to represent a single subject genome.

One embodiment of the present invention can include a method of representing a subject genome. The method can include comparing the subject genome to a base reference genome and identifying a difference between the subject genome and the base reference genome. One or more items of descriptive information can be assigned to the difference. The items of descriptive information can be compiled into a data set representing the subject genome.

Another embodiment of the present invention can include a system for representing a subject genome. The system can include a comparator configured to compare a reference genome with a subject genome. The comparator can identify one or more differences between the subject genome and the reference genome. The comparator also can ascribe one or more items of descriptive information to each difference.

Other embodiments of the present invention can include a machine readable storage programmed to cause a machine to perform the steps described herein.

BRIEF DESCRIPTION OF THE DRAWINGS

There are shown in the drawings, embodiments that are presently preferred; it being understood, however, that the invention is not limited to the precise arrangements and instrumentalities shown.

DETAILED DESCRIPTION OF THE INVENTION

Figure 1:
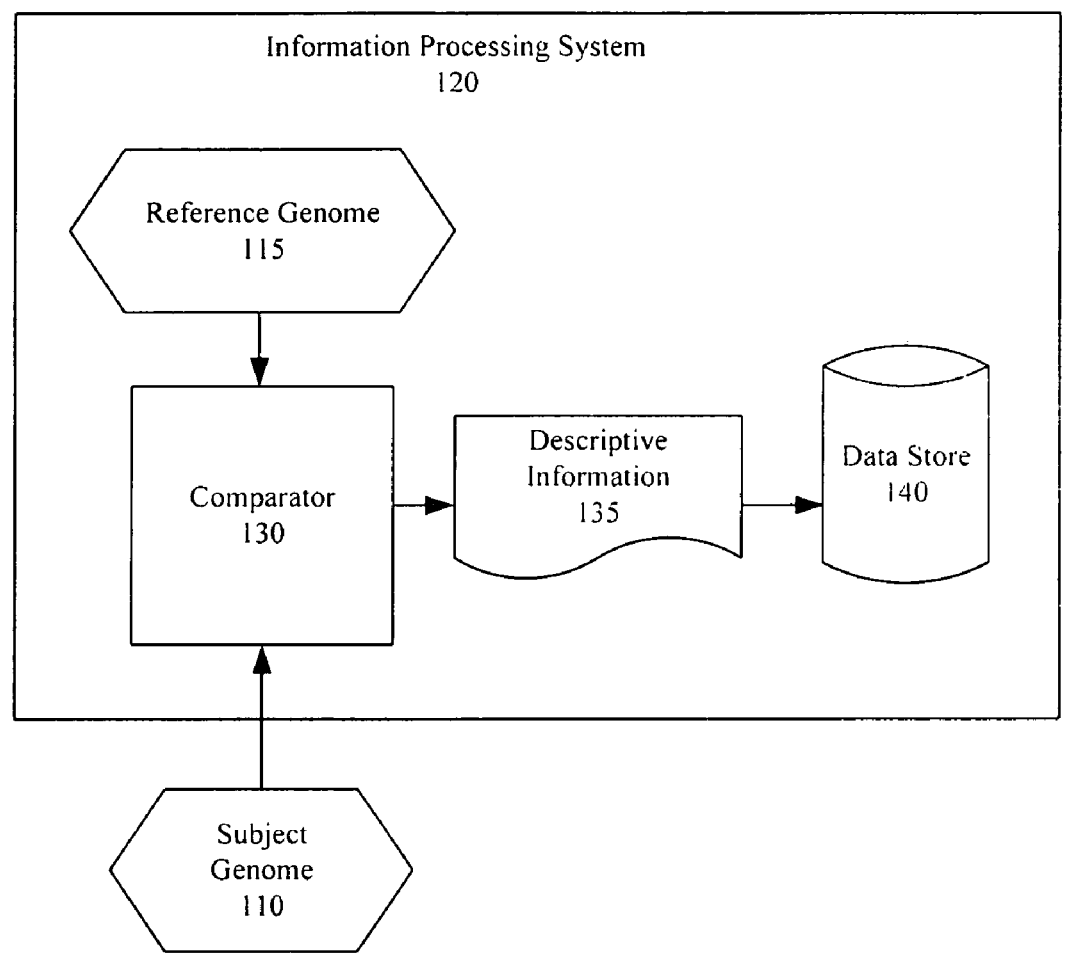
FIG. 1 is a schematic diagram illustrating a system for representing a subject genome as a set of differences between a reference genome and the subject genome in accordance with one embodiment of the present invention.

FIG. 1 is a schematic diagram illustrating a system 100 for representing a subject genome as a set of differences between a reference genome and the subject genome in accordance with one embodiment of the present invention. As shown the system 100 can include an information processing system 120. The information processing system 120 can be implemented as any type of computer system such as a home or personal computer system, a portable computer, a desktop computer or other information processing device that can execute the functions described herein. For example, in one embodiment, the information processing system 120 can be an integrated system, such as the IBM Life Sciences Clinical Genomics Solution, which can include the IBM DB2® Universal Database™ software, the IBM @server® pSeries® server and the IBM TotalStorage® data storage.

Generally, human genomes differ from each other about once every 1,000 nucleotide bases. These variations, known as single nucleotide polymorphisms (SNPs). add up to a total of about 3,000,000 differences between any two human genomes. Accordingly, a base reference genome 115 can be constructed which can provide a model genome for comparison purposes. The base reference genome 115 can be stored within the information processing system 120, or in another network location that is accessible to the information processing system 120.

The information processing system 120 can include a comparator 130 and a data store 140. The comparator 130 can be a software application executing within the information processing system 120. According to one embodiment of the present invention, the comparator 130 can compare a subject genome 110 to the base reference genome 115. The comparator 130 can identify one or more variations or differences between the subject genome 110 and the base reference genome 115. The comparator 130 can assign to each difference between the subject genome 110 and the reference genome 115 one or more items of descriptive information 135. The items of descriptive information 135 can define the type of difference as well as the approximate location of the difference in relation to the reference genome 115.

In one embodiment, the items of descriptive information 135 can be compiled into a data set which can represent the subject genome 110. The data set can be stored within the data store 140. Notably, while the comparator 130 and data store 140 are depicted as being located within the information processing system 120, it should be appreciated that each component can be implemented in one or more information processing systems in a distributed fashion. Further, the comparator 130, while represented as a single application program, can be implemented as a combination of one or more application programs.

Figure 2:
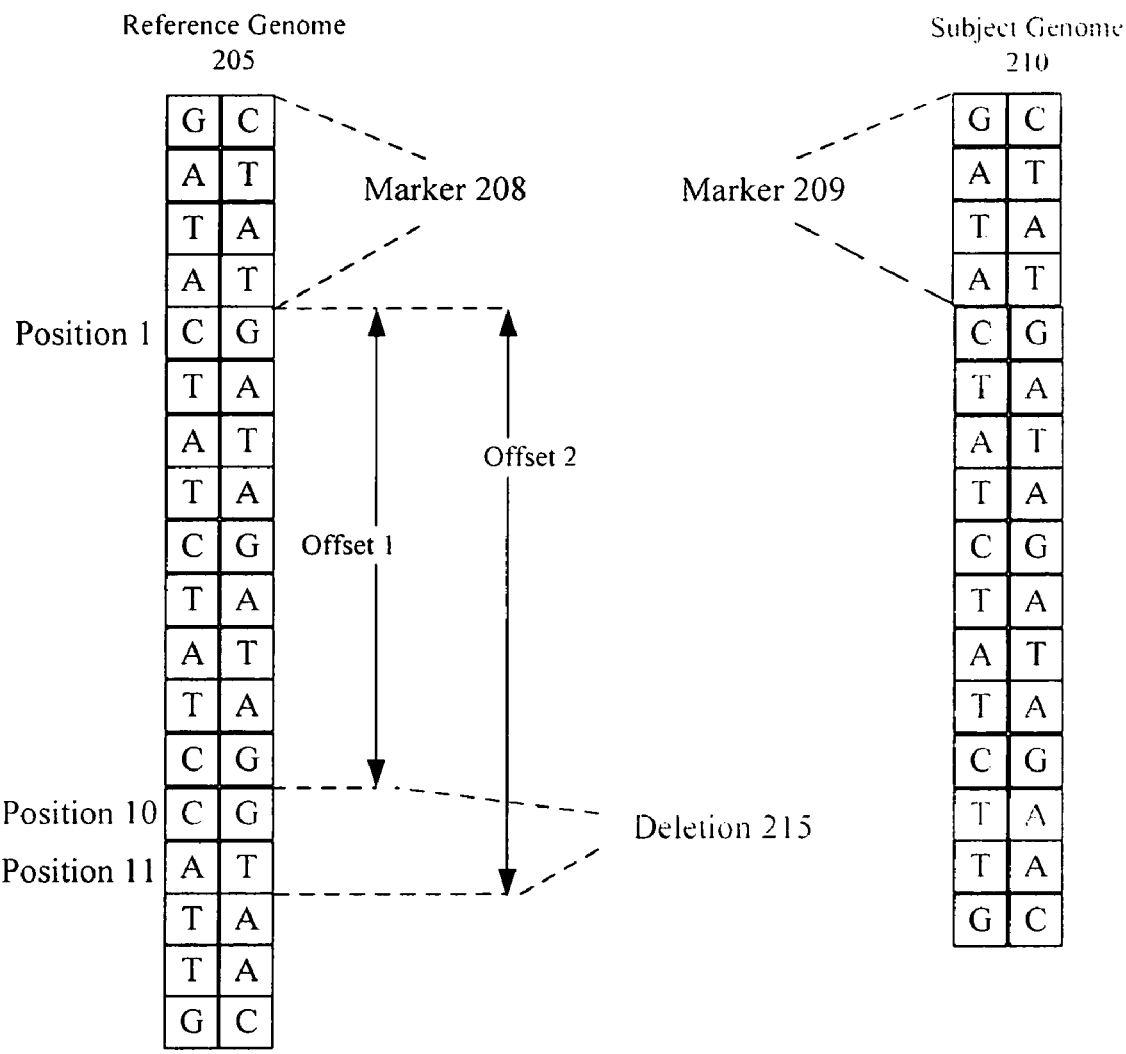
FIG. 2 is a schematic diagram illustrating a comparison of a subject genome to a reference genome in accordance with another embodiment of the present invention.

FIG. 2 is a schematic diagram illustrating a comparison of a subject genome to a reference genome in accordance with another embodiment of the present invention. FIG. 2 depicts a reference genome 205 and a subject genome 210. As noted, a genome is a string of DNA. A DNA molecule consists of two strands that wrap around each other to resemble a twisted ladder. The sides of the "ladder" are comprised of sugar and phosphate molecules. The "rungs" of the genome, which are illustrated in FIG. 2, are comprised of the chemicals adenine (A), thymine (T), cytosine (C), and guanine (G). These chemicals, also known as bases or nucleotides, pair together in a particular manner. That is, A pairs only with T, and C pairs only with G. The particular order of these nucleotide pairs is known as the DNA sequence, which specifies the exact genetic instructions required to create a particular organism with its own traits.

Although it is estimated that a human genome consists of approximately 3 billion nucleotides and 30,000 genes, the genomes among humans are sufficiently similar such that it is possible to construct a base reference genome, such as reference genome 205. In one aspect of the present invention, the reference genome 205 can be compared with the subject genome 210. Only the variations between the two genomes can be recorded and compiled to represent the subject genome 210.

A listing of such variations or differences can include, but is not limited to, deletions, additions, translocations, and SNP's. A deletion occurs when a nucleotide base is not found in the subject genome 210, but is found within the reference genome 205. An addition occurs when a nucleotide base is discovered in the subject genome 210 that is not in the base reference genome 205. A translocation occurs when a nucleotide sequence is found in both the subject genome 210 and the reference genome 205 but in different locations. Translocations can form when a large segment of DNA breaks off or is removed from one chromosome, and attaches to another chromosome.

An SNP can be a one nucleotide variation between the subject genome and the reference genome. As noted, it is estimated that an SNP occurs about once in every 1,000 nucleotide bases. Researchers have identified about 1.4 million locations where SNPs occur in human genomes. Another variation which can exist between the reference genome 205 and the subject genome 210 can be a discrepancy in the repeat count of a single nucleotide sequence, or micro-satellite, between the subject genome and the reference genome. Still, as noted, it should be appreciated that other types of variations between the reference genome 205 and the subject genome 210 can exist and be identified.

In one aspect of the present invention, an information processing system configured as described herein can determine and store items of descriptive information regarding a variation identified between the reference genome 205 and the subject genome 210. In one embodiment, a marker on the reference genome 205 which is nearest to the difference can be identified. A marker is a segment of DNA, such as a gene or a section of "junk DNA", which has an identifiable physical location on a chromosome and whose inheritance can be followed. There are several types of markers used in DNA studies. For example, there are more than 30,000 identified gene markers. Alternatively, a micro-satellite, which consists of repetitive stretches of short sequences of DNA as short as 2 base pairs long, can form a marker. To date researchers have identified approximately 15,000 micro-satellite markers. Notably, DNA segments that lie near each other on a chromosome tend to be inherited together. Therefore markers can be used to track the inheritance pattern of genes that have not yet been identified but whose approximate locations are known.

For example, FIG. 2 depicts a genetic marker 208 which is located on the reference genome 205, and has been identified as the marker closest to a deletion 215. The deletion 215 refers to two nucleotide base pairs found within the reference genome 205 that are not present in the subject genome 210. Notably, the subject genome 210 can contain a marker 209 that is the same as or corresponds to marker 208. As is known in the art, each genetic marker is designated by a number according to international conventions. The information processing system can assign marker 208's official number as an item of descriptive information to the identified difference. Still, the present invention is not so limited as any type of indicator or label can be used.

In another embodiment of the present invention, the information processing system can determine one or more offsets in order to approximate the location of the difference with reference to the reference genome 205. In operation, the information processing system can compare portions of DNA of the reference genome 205 in and around the marker 208 with portions of DNA of the subject genome 210 in and around marker 209 in order to determine the starting and ending points of the difference. For example, in FIG. 2, the starting point of the deletion 215 is located at position 10 from the marker 208, and the ending point of deletion 215 is located at position 11 from the marker 208. Accordingly, an offset can be determined from the marker to the starting point and/or the ending point of the difference. Notably, an offset can be described in one of two directions, 3' and 5', where 5' refers to the leading end of a strand of nucleic acid and 3' refers to the tail end.

Identifying both the starting and ending points can allow for deletions and insertions into the reference genome 205. Similar to the marker number, the information processing system can assign one or more offset values to the identified difference as items of descriptive information. Additional items of descriptive information can include, but are not limited to, the difference between a number of repeat counts the locations pertaining to a translocation, the nucleotide bases that have been added or deleted in reference to the reference genome 205, and/or information pertaining to or describing an SNP.

One skilled in the art will recognize that the various DNA configurations disclosed herein can be embodied in various other forms and that the configuration disclosed and described with reference to FIG. 2 is provided for purposes of illustration only. For example, the difference or variation between the reference genome 205 and the subject genome 210 can exist within the marker, such as within a gene or a micro-satellite. In this case, the information processing system can determine the location of the variation within the marker. Notably, within markers mutations can occur at random and it is estimated that any given marker has a 0.002 chance of mutating with each generation.

In one embodiment of the present invention, the information processing system can assign a text description to the difference as an item of descriptive information. That is, the text description can describe the difference identified between the reference genome and the subject genome. In the case of the example depicted in FIG. 2, the text description of the difference can include the word "deletion." Other text descriptions can include, but are not limited to, "addition", "translocation", "SNP", and/or "repeat" indicating a discrepancy in the number of a repeat count. It should be appreciated that a variety of information can be included in the text description and that the examples disclosed herein are not intended as limitations of the present invention. Rather, the examples disclosed herein are intended to broaden the scope of the present invention.

Figure 3:
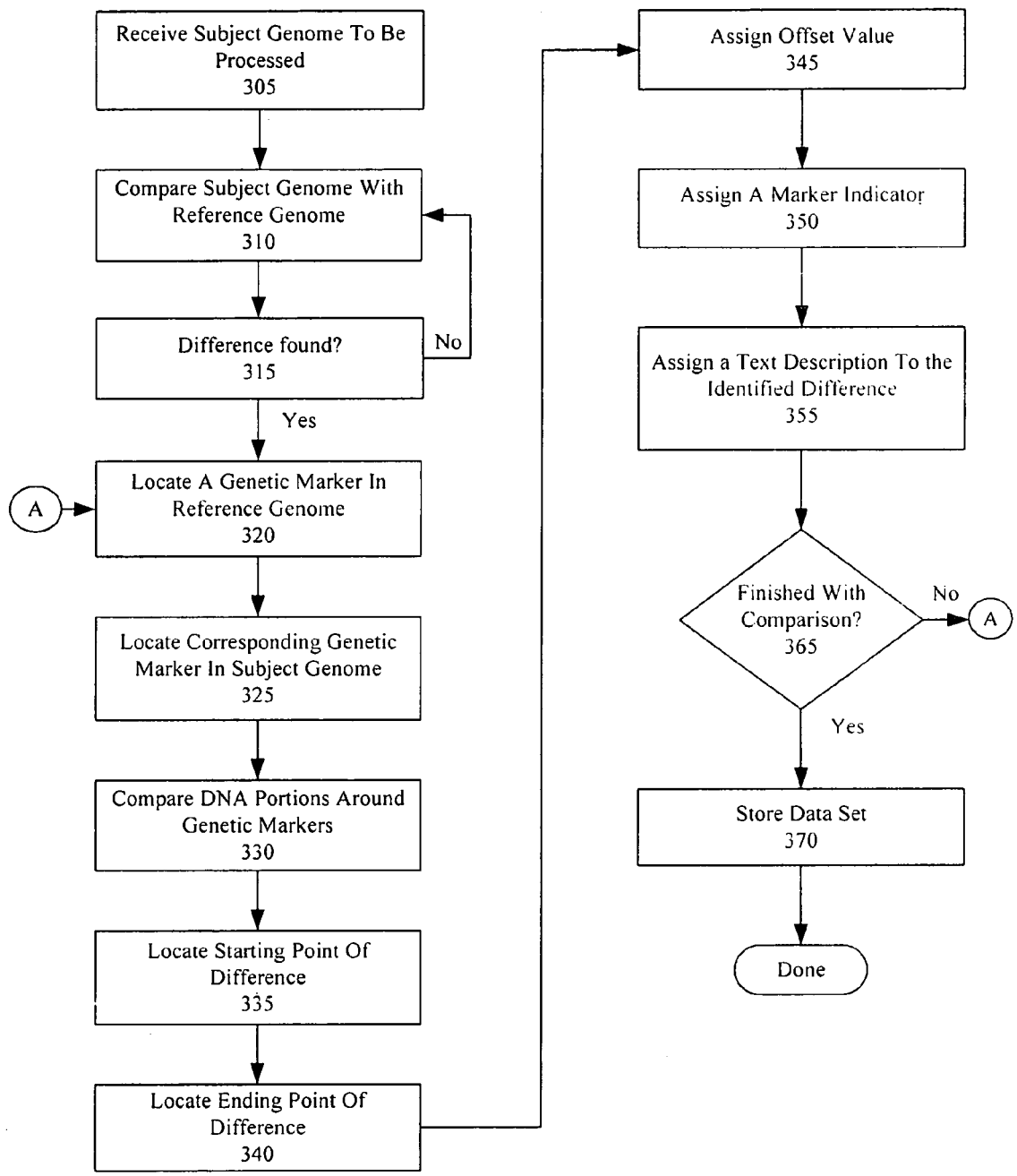
FIG. 3 is a flow chart illustrating a method of representing a subject genome as a set of differences between a reference genome and the subject genome in accordance with yet another embodiment of the present invention.

FIG. 3 is a flow chart illustrating a method 300 of representing a subject genome as a set of differences between a reference genome and a subject genome in accordance with yet another embodiment of the present invention. The method 300 can be used to identify one or more differences between a subject and reference genome, assign items of descriptive information to each difference, and compile the items into a single data set. Accordingly, the resulting data set can represent the subject genome and be stored in a data store to facilitate genetic research.

The method 300 can begin in step 305 where a subject genome to be processed can be received and/or loaded. In step 310, the subject genome can be compared with a reference genome. In step 315, a determination can be made as to whether a difference between the subject genome and the reference genome has been found. If so, the method can proceed to step 320. If not, the method can loop back to step 310 to continue comparing the two genomes.

In step 320, in response to the identification of a difference, a marker can be located within the reference genome which can be the closest well-known marker to the difference. In step 325, a corresponding marker can be located in the subject genome. In step 330, the information portions of DNA around the genetic markers identified in steps 320 and 325 can be compared. In step 335, a starting point of the variation of the subject genome as compared to the reference genome can be located and an offset value can be calculated with reference to the marker in the reference genome. Similarly, in step 340, an ending point of the variation between the subject genome and the reference genome can be located and a second or ending offset value can be calculated within the reference to the marker of the reference genome. In step 345, one or more offset values can be associated with, or assigned to, the difference. As noted, the offset can be in one of two directions, namely, 3' or 5'.

It should be appreciated that a difference can be identified which is located within the marker itself. In this case, only the portions of DNA within the marker need to be compared in order to determine the position of the variation within the marker.

In step 350, a label or indicator can be assigned to the difference. As noted, the indicator can be the marker number or other identifier. Similarly, in step 355, the method can assign a text description of the difference. For example, the text description can include, among other data, the type of difference, such as an addition, deletion. translocation, SNP, and/or a repetitive micro-satellite. Notably, the text description can include a variety of genetic information and is not limited to the type of difference.

In step 365, if the comparison of the reference genome and the subject genome is finished, the method can continue to step 370. If not, however, the method can loop back to step 320 and continue processing. In step 370, the accumulated data, i.e. any indicators or marker numbers, text labels, starting and/or ending offsets, translocation information, and/or other information can be stored. It should be appreciated that all data pertaining to a particular variation or difference between the subject genome and the reference genome can be associated, for example as a single entry describing that difference. The entire set of descriptive data can specify the subject genome. Notably, while the method 300 indicates that data is stored when the comparison is finished it should be appreciated that data also can be stored as it is determined. For example, in another embodiment, data relating to a particular difference can be stored once determined and prior to processing or analyzing another difference. After step 370, the method can end.

One benefit of the present invention can include reducing the storage requirement necessary to store genomic information by representing a subject genome as a set of differences between a reference genome and the subject genome. The gene coding method described herein also can offer additional benefits. For example a variation located close to or within a gene is more likely to affect the operation oil that same gene. Therefore, each difference mapped relative to a known gene coding sequence may provide researchers with insight as to the significance of the difference.

The present invention can be realized in hardware, software, or a combination of hardware and software. The present invention can be realized in a centralized fashion in one computer system or in a distributed fashion where different elements are spread across several interconnected computer systems. Any kind of computer system or other apparatus adapted for carrying out the methods described herein is suited. A typical combination of hardware and software can be a general-purpose computer system with a computer program that, when being loaded and executed, controls the computer system such that it carries out the methods described herein.

The present invention also can be embedded in a computer program product which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

This invention can be embodied in other forms without departing from the spirit or essential attributes thereof. Accordingly, reference should be made to the following claims, rather than to the foregoing specification, as indicating the scope of the invention.

What is claimed is:

1. A method of compactly representing and storing a complete subject genome comprising:
   programming a computer to carry out the following steps:
      constructing a base reference genome for a species, wherein said base reference genome is a benchmark or model genome for the species;
      providing the subject genome, said subject genome being a genome of a member of the species;
      retrieving the base reference genome;
      comparing the subject genome to the base reference genome;
      identifying all differences between the subject genome and the base reference genome;
      assigning one or more items of descriptive information to each of the differences, wherein each of said items of descriptive information describes a particular deviation of the subject genome from the base reference genome resulting in each of said differences;
      compiling the items of descriptive information describing all the differences between the subject genome and the base reference genome into a data set, wherein the data set represents the complete subject genome, and wherein the data set does not include data other than the items of descriptive information describing each difference between the subject genome and the base reference genome; and
      storing the data set representing the complete subject genome on a machine readable storage; and
   using the stored data set for genetic research or medical treatment.

2. The method of claim 1, wherein the difference is a nucleotide in the subject genome that is not in the base reference genome or is a nucleotide that is not in the subject genome that is in the base reference genome.

3. The method of claim 1, wherein the difference is a nucleotide sequence contained in both the subject genome and the base reference genome but which is situated in different locations.

4. The method of claim 1, wherein the difference is a single nucleotide polymorphism.

5. The method of claim 1, wherein the difference is a discrepancy in the repeat count of a micro-satellite between the subject genome and the base reference genome.

6. The method of claim 1, said step of assigning an item of descriptive information further comprising:
   identifying a position reference point in the base reference genome;
   locating a corresponding position reference point in the subject genome; and
   assigning a description to the difference.

7. The method of claim 6, wherein the position reference point is a gene marker.

8. The method of claims 6, wherein the position reference point is a micro-satellite marker.

9. The method of claim 6, further comprising:
   comparing portions of DNA around the position reference point;
   locating a starting point of the difference;
   determining an ending point of the difference; and
   calculating one or more offset values based on the starting and ending points.

10. A system for compactly representing and storing a complete subject genome comprising:
    a computer programmed to:
       construct a base reference genome for a species, wherein said base reference genome is a benchmark or model genome for the species;
       obtain the subject genome, said subject genome being a genome of a member of the species;
       retrieve the base reference genome;
       compare the subject genome to the base reference genome;
       identify all differences between the subject genome and the base reference genome;
       assign one or more items of descriptive information to each of the differences, wherein each of said items of descriptive information describes a particular deviation of the subject genome from the base reference genome resulting in each of said differences;
       compile the items of descriptive information describing all the differences between the subject genome and the base reference genome into a data set,
    wherein the data set represents the complete subject genome and wherein the data set does not include data other than the items of descriptive information describing each difference between the subject genome and the base reference genome; and
    store the data set representing the complete subject genome on a machine readable storage, wherein the stored data set is used for genetic research or medical treatment.

11. A machine readable storage, having stored thereon a computer program having a plurality of code sections executable by a machine for causing the machine to perform the steps of:
    constructing a base reference genome for a species, wherein said base reference genome is a benchmark or model genome for the species;
    providing the subject genome, said subject genome being a genome of a member of the species;
    retrieving the base reference genome;
    comparing the subject genome to the base reference genome;
    identifying all differences between the subject genome and the base reference genome;
    assigning one or more items of descriptive information to each of the differences, wherein each of said items of descriptive information describes a particular deviation of the subject genome from the base reference genome resulting in each of said differences;
    compiling the items of descriptive information describing all the differences between the subject genome and the base reference genome into a data set, wherein the data set represents the complete subject genome, and wherein the data set does not include data other than the items of descriptive information describing each difference between the subject genome and the base reference genome; and
    storing the data set representing the complete subject genome on a machine readable storage, wherein the stored data set is used for genetic research or medical treatment.

12. The machine readable storage of claim 11, wherein the difference is a nucleotide in the subject genome that is not in the base reference genome or a nucleotide that is not in the subject genome that is in the base reference genome.

13. The machine readable storage of claim 11, wherein the difference is a nucleotide sequence contained in both the subject genome and the base reference genome but which is situated in different locations.

14. The machine readable storage of claim 11, wherein the difference is a single nucleotide polymorphism.

15. The machine readable storage of claim 11, wherein the difference is a discrepancy in the repeat count of a micro-satellite between the subject genome and the base reference genome.

16. The machine readable storage of claim 11, said step of assigning one or more items of descriptive information further comprising:
   identifying a position reference point in the base reference genome;
   locating a corresponding position reference point in the subject genome; and
   assigning a text description to the difference.

17. The machine readable storage of claim 16, wherein the position reference point is a gene marker.

18. The machine readable storage of claim 16, wherein the position reference point is a micro-satellite marker.

19. The machine readable storage of claim 16, further comprising:
   comparing portions of DNA around the position reference point;
   locating a starting point of the difference;
   determining an ending point of the difference; and
   calculating one or more offset values based on the starting and ending points.

\* \* \* \* \*

UNITED STATES PATENT AND TRADEMARK OFFICE
CERTIFICATE OF CORRECTION

PATENT NO. : 7,657,383 B2　　　　　　　　　　　　　　　　　　　　　Page 1 of 1
APPLICATION NO. : 10/856600
DATED : February 2, 2010
INVENTOR(S) : Allard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 542 days.

Signed and Sealed this

Thirtieth Day of November, 2010

David J. Kappos
*Director of the United States Patent and Trademark Office*